(12) United States Patent
Nigam et al.

(10) Patent No.: US 8,024,031 B2
(45) Date of Patent: Sep. 20, 2011

(54) DEVICE, METHOD AND COMPUTER-READABLE STORAGE MEDIUM FOR CLASSIFYING ATRIAL TACHYARRHYTHMIA

(75) Inventors: Indra B. Nigam, Tigard, OR (US); Dirk Muessig, West Linn, OR (US); Hannes Kraetschmer, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 584 days.

(21) Appl. No.: 12/254,728

(22) Filed: Oct. 20, 2008

(65) Prior Publication Data

US 2010/0100143 A1    Apr. 22, 2010

(51) Int. Cl.
A61B 5/04    (2006.01)
(52) U.S. Cl. ............... 600/518; 600/515; 607/4
(58) Field of Classification Search .......... 600/515, 600/518; 607/2, 9, 14
See application file for complete search history.

(56) References Cited

U.S. PATENT DOCUMENTS

| | | | |
|---|---|---|---|
| 4,880,005 A | | 11/1989 | Pless et al. |
| 5,161,527 A | * | 11/1992 | Nappholz et al. ............ 607/14 |
| 5,205,283 A | | 4/1993 | Olson |
| 5,251,621 A | | 10/1993 | Collins |
| 5,788,717 A | * | 8/1998 | Mann et al. ................ 607/14 |
| 5,817,134 A | * | 10/1998 | Greenhut et al. ............ 607/14 |
| 5,893,882 A | | 4/1999 | Peterson et al. |
| 5,941,831 A | | 8/1999 | Turcott |
| 6,671,548 B1 | * | 12/2003 | Mouchawar et al. .......... 607/14 |
| 7,580,740 B2 | * | 8/2009 | Kim et al. ................... 600/515 |
| 2006/0167520 A1 | | 7/2006 | Gilkerson et al. |
| 2006/0259089 A1 | | 11/2006 | Kim et al. |

OTHER PUBLICATIONS

European Search Report for Application No. 09 17 2864, dated Feb. 8, 2010, 6 pages.
European Search Report for Application No. 09 17 2864.2, dated Mar. 22, 2010, 10 pages.

* cited by examiner

*Primary Examiner* — Brian T Gedeon
(74) *Attorney, Agent, or Firm* — ARC IP Law, PC; Joseph J. Mayo

(57) ABSTRACT

Device for classifying tachyarrhythmia that obtains pre-defined values, monitors atrial intervals and compares lengths of each interval with pre-defined value IL, stores length of atrial interval if length is shorter than IL, in case X of most recent Y number of atrial intervals have length shorter than IL, evaluates most recent <=N atrial intervals with length <IL and performs test for stored lengths via criteria, classifies atrial tachyarrhythmia as stable if all tested lengths pass >=1 criteria, and controls a cardiac device depending on the classification. Atrial intervals are first evaluated by using the "X-out-of-Y" criterion and subsequently checked for stability after an atrial tachyarrhythmia is detected using "X-out-of-Y" criterion. For stability check, only intervals found shorter than the interval limit are used. Check is based on interval-to-interval comparison rather than as generally practiced, comparisons of individual intervals with the minimum or average of all intervals.

25 Claims, 5 Drawing Sheets

DEVICE, METHOD AND COMPUTER-READABLE STORAGE MEDIUM FOR CLASSIFYING ATRIAL TACHYARRHYTHMIA

BACKGROUND OF THE INVENTION

1. Field of the Invention

The present invention generally relates to implantable cardiac devices, including pacemakers, defibrillators and cardioverters, which stimulate cardiac tissue electrically to control the patient's heart rhythm. More particularly, the present invention relates to a method and device for classifying atrial tachyarrhythmia as being stable or unstable. Further, the present invention relates to a method and device for indicating Very High Rate rhythm.

2. Description of the Related Art

There are previously proposed methods for detecting atrial tachyarrhythmias and a determination of their being stable or unstable. However, an otherwise simple task is complicated by the fact that a multi-chamber pacemaker or ICD may not "see" all of the atrial complexes due to some of these falling in cross-chamber blanking periods, such as post-ventricular-pace blanking and far-field blanking periods.

It is known from the prior art to use a so called "X-out-of-Y" criterion to detect an ongoing atrial tachyarrhythmia. The U.S. Pat. No. 6,671,548 B1 for example describes use of such a "X-out-of-Y" criterion. This criterion declares detection of an atrial tachyarrhythmia when X number of intervals among most recent Y number of atrial intervals are found to be shorter than an interval limit corresponding to the tachyarrhythmia rate limit. The numbers X, Y and the tachyarrhythmia rate limit may be user defined, e.g., pre-defined or may be programmable. As is clear, the "X-out-of-Y" criterion accommodates for undersensing of some of the atrial events.

BRIEF SUMMARY OF THE INVENTION

It is an objective of the invention to provide a device, for example an implantable cardiac device, such as a pacemaker, a defibrillator or a cardioverter, for classifying tachyarrhythmia. The device comprises control and storage means and is arranged for executing a method for classifying atrial tachyarrhythmia, the method comprising the following steps:

a) obtaining pre-defined numbers N, X and Y with $N \leq X < Y$;

b) monitoring atrial intervals and comparing the length of each interval with a pre-defined value IL;

c) storing the length of atrial interval if the length is shorter than IL;

d) in case X among the most recent Y number of atrial intervals are found to have a length shorter than IL evaluating the most recent up to N atrial intervals which have a length shorter than IL by performing for each of the stored length a test with respect to the following criteria:

the absolute value of the difference between the stored length and its preceding stored length does not exceed a pre-defined value SL, the absolute value of the difference between twice the stored length and one time of the preceding stored length does not exceed the double of the value SL, and the absolute value of the difference between the stored length and twice the preceding stored length does not exceed the double of the value SL;

e) classifying the atrial tachyarrhythmia as stable if all of the tested lengths pass at least one of the criteria; and f) controlling a cardiac device depending on the classification.

According to this method atrial intervals are first evaluated by using the "X-out-of-Y" criterion and subsequently checked for stability after an atrial tachyarrhythmia has been detected using the "X-out-of-Y" criterion.

An advantage of the present invention lies in the way the determination of the rhythm's stability is made. For the stability check, only those intervals that were found to be shorter than the said interval limit are used; more specifically, only the most recent N, for example 8, of such intervals are used. The stability check, itself, is based on an interval-to-interval comparison rather than—as generally practiced—comparisons of individual intervals with the minimum or average of all used intervals.

In a preferred embodiment of the inventive method it is proposed to use a first FIFO buffer of size Y and to push a first flag indicating tachyarrhythmia in the first FIFO buffer if the length of the monitored atrial interval is shorter than IL, and to push a second flag indicating non-tachyarrhythmia in the first FIFO buffer if the length of the monitored atrial interval is equal to or longer than IL. Preferably the first flag is a binary "1", and the second flag is a binary "0".

It is also proposed to use a counter to check compliance with the "X-out-of-Y" criterion. The counter is incremented by 1 if the monitored atrial interval has a length shorter than IL, and which is decremented by 1 if the atrial interval at the Yth position before the monitored atrial interval has a length shorter than IL.

It is further proposed to store the lengths shorter than IL in the second FIFO buffer of size N, which is treated as a ring buffer when testing the stored atrial intervals for stability. Due to the ring buffer property individual checks for each length stored in the ring buffer can be easily performed for all of the most recent N intervals with length shorter than IL. For that the stored length of the most recent atrial interval is also used as length preceding the oldest stored length.

A further objective of the invention is to provide a method for detection of Very High Rate rhythm of an atrial tachyarrhythmia. This may be carried out after detection of atrial tachy-arrhythmia with or without a stability test. For testing for Very High Rate rhythm a Very High Rate Interval Limit VHRIL and numbers X1 and Y1 (X1<Y1) for another "X1-out-of-Y1" criterion. Very High Rate rhythm detection comprises comparison of the length of the most recent Y1 number of atrial intervals which have a length shorter than IL with VHRIL and indicating Very High Rate rhythm for the detected tachyarrhythmia if a number of X1 lengths shorter than VHRIL are found. X1 may be set, for example, to 3.

If both tests, stability test and Very High Rate test, are performed, for the Very High Rate test preferably only those intervals are used, which are used for the stability test, thus setting Y1 equal to N. Using this indication, an otherwise stable but Very High Rate atrial tachyarrhythmia may optionally be classified as atrial fibrillation. Optionally atrial tachyarrhythmia may be classified as fibrillation regardless of stability if Very High Rate rhythm is indicated.

In another preferred embodiment a Very High Rate test is performed without considering stability. The method for classifying atrial tachyarrhythmia comprising the following steps:

a) obtaining pre-defined numbers X, X1, Y and Y1 with X<Y and X1<Y1;

b) monitoring atrial intervals and comparing the length of each atrial interval with a pre-defined value IL;

c) in case X among the most recent Y number of atrial intervals are found to have a length shorter than IL comparing the lengths of the most recent Y1 number of atrial intervals which have a length shorter than IL with a pre-defined value VHRIL;

d) classifying Very High Rate rhythm if X1 out of the Y1 number of atrial intervals which have a length shorter than IL are found having a length shorter than VHRIL; and e) controlling a cardiac device depending on the classification.

In a further step atrial tachyarrhythmia may be classified as fibrillation if Very High Rate rhythm is indicated.

For the VHR check, only those intervals that were found to be shorter than the said interval limit are used; more specifically, only the most recent Y1, for example 8, of such intervals are used. X1 may be set, for example, to 3.

In a preferred embodiment of the inventive method it is also proposed to use a first FIFO buffer of size Y and to push a first flag indicating tachyarrhythmia in the first FIFO buffer if the length of the monitored atrial interval is shorter than IL, and to push a second flag indicating non-tachyarrhythmia in the first FIFO buffer if the length of the monitored atrial interval is equal to or longer than IL. Preferably the first flag is a binary "1", and the second flag is a binary "0".

Further it is also proposed to use a counter to check compliance with the "X-out-of-Y" criterion. The counter is incremented by 1 if the monitored atrial interval has a length shorter than IL, and which is decremented by 1 if the atrial interval at the Yth position before the monitored atrial interval has a length shorter than IL.

It is another objective of the invention to provide a device for classifying atrial tachyarrhythmia comprising control and storage means, the device being arranged for executing a method for classifying atrial tachyarrhythmia, the method comprising the following steps:

a) obtaining pre-defined numbers N, X and Y with $N \leq X < Y$;

b) monitoring atrial intervals and comparing the length of each interval with a pre-defined value IL;

c) storing the length of atrial interval if the length is shorter than IL;

d) in case X among the most recent Y number of atrial intervals are found to have a length shorter than IL evaluating the most recent up to N atrial intervals which have a length shorter than IL by performing for each of the stored length a test with respect to the following criteria:

the absolute value of the difference between the stored length and its preceding stored length does not exceed a pre-defined value SL, the absolute value of the difference between twice the stored length and one time of the preceding stored length does not exceed the double of the value SL, and the absolute value of the difference between the stored length and twice the preceding stored length does not exceed the double of the value SL;

e) classifying the atrial tachyarrhythmia as stable if all of the tested lengths pass at least one of the criteria; and f) controlling a cardiac device depending on the classification.

The device may be an implantable cardiac device, such as a pacemaker, a defibrillator or a cardioverter.

With respect to terminology utilized herein, "means for" as utilized herein may signify either a specific apparatus component detailed herein or may alternatively signify a shorthand for a corresponding "means", i.e., "storage means for storing" may simply be interpreted as "storage means configured to store", etc., in ANY storage means that one skilled in the art would substitute whether or not specified herein.):

In a preferred embodiment the device comprises, storage means for storing the pre-defined values IL, N, SL, X and Y;

means for monitoring cardiac events;

means for deciding whether an atrial interval has a length shorter than IL or not, the means for deciding being communicatively connected with the storage means and the means for monitoring;

a first FIFO buffer of size Y communicatively connected with the means for deciding for storing flags indicating whether an atrial interval has a length shorter than IL or not;

a counter communicatively connected with the means for monitoring and with the first FIFO buffer for counting atrial intervals with a length shorter than IL among the most recent Y number of atrial intervals;

a second FIFO buffer of size N communicatively connected with the means for deciding for storing the length of atrial interval if the length is shorter than IL; and processing means communicatively connected with the storage means, with the counter and with the second FIFO buffer for performing the test and for controlling the device.

Preferably, the second FIFO buffer is treated at least temporarily as a ring buffer.

It is a further objective of the invention to provide a device for classifying atrial tachyarrhythmia comprising control and storage means, the device being arranged for executing a method for classifying atrial tachyarrhythmia, the method comprising the following steps:

a) obtaining pre-defined numbers X, X1, Y and Y1 with $X<Y$ and $X1<Y1$;

b) monitoring atrial intervals and comparing the length of each atrial interval with a pre-defined value IL;

c) in case X among the most recent Y number of atrial intervals are found to have a length shorter than IL comparing the lengths of the most recent Y1 number of atrial intervals which have a length shorter than IL with a pre-defined value VHRIL;

d) classifying Very High Rate rhythm if X1 out of the Y1 number of atrial intervals which have a length shorter than IL are found having a length shorter than VHRIL; and e) controlling a cardiac device depending on the classification.

Also this device may be an implantable cardiac device, such as a pacemaker, a defibrillator or a cardioverter.

In a preferred embodiment the device comprises:

storage means for storing the pre-defined values IL, X, X1, Y, Y1 and VHRIL;

means for monitoring cardiac events;

means for deciding whether an atrial interval has a length shorter than IL or not, the means for deciding being communicatively connected with the storage means and the means for monitoring;

a first FIFO buffer of size Y communicatively connected with the means for deciding for storing flags indicating whether an atrial interval has a length shorter than IL or not;

a counter communicatively connected with the means for monitoring and with the first FIFO buffer for counting atrial intervals with a length shorter than IL among the most recent Y number of atrial intervals;

a second FIFO buffer of size Y1 communicatively connected with the means for deciding for storing the length of atrial interval if the length is shorter than IL; and processing means communicatively connected with the storage means, with the counter and with the second FIFO buffer for classifying Very High Rate rhythm and for controlling the device.

A further objective of the invention is to provide a computer-readable storage medium storing program code for causing a data processing device to perform a method for classifying atrial tachyarrhythmia, the method comprising the steps of:

a) obtaining pre-defined numbers N, X and Y with $N \leq X < Y$;

b) monitoring atrial intervals and comparing the length of each interval with a pre-defined value IL;

c) storing the length of atrial interval if the length is shorter than IL;

d) in case X among the most recent Y number of atrial intervals are found to have a length shorter than IL evaluating the most recent up to N atrial intervals which have a length shorter than IL by performing for each of the stored length a test with respect to the following criteria:

the absolute value of the difference between the stored length and its preceding stored length does not exceed a pre-defined value SL, the absolute value of the difference between twice the stored length and one time of the preceding stored length does not exceed the double of the value SL, and the absolute value of the difference between the stored length and twice the preceding stored length does not exceed the double of the value SL;

e) classifying the atrial tachyarrhythmia as stable if all of the tested lengths pass at least one of the criteria; and f) controlling a cardiac device depending on the classification.

According to a further aspect of the invention there is provided another computer-readable storage medium storing program code for causing a data processing device to perform a method for classifying atrial tachyarrhythmia, the method comprising the steps of:

a) obtaining pre-defined numbers X, X1, Y and Y1 with $X < Y$ and $X1 < Y1$;

b) monitoring atrial intervals and comparing the length of each atrial interval with a pre-defined value IL;

c) in case X among the most recent Y number of atrial intervals are found to have a length shorter than IL comparing the lengths the most recent Y1 number of atrial intervals which have a length shorter than IL with a pre-defined value VHRIL;

d) classifying Very High Rate rhythm if X1 out of the Y1 number of atrial intervals which have a length shorter than IL are found having a length shorter than VHRIL; and e) controlling a cardiac device depending on the classification.

The details of the invention can be understood from the following drawings and the corresponding text descriptions.

The innovation of the present invention lies in the way the determination of the rhythm's stability is made. For the stability check, only those intervals that were found to be shorter than the said interval limit are used; more specifically, only the most recent 8 of such intervals are used. The stability check, itself, is based on an interval-to-interval comparison rather than—as generally practiced—comparisons of individual intervals with the minimum or average of all used intervals.

Finally, an indication of the detected tachyarrhythmia being a Very High Rate rhythm is set based on another "X1-out-of-Y1' criterion that uses only those intervals, which are used for the stability check, and that uses an interval limit corresponding to another [programmable] rate limit. Using this indication, an otherwise stable but Very High Rate atrial tachyarrhythmia may optionally be classified as atrial fibrillation.

DETAILED DESCRIPTION OF THE INVENTION

Figure 1:
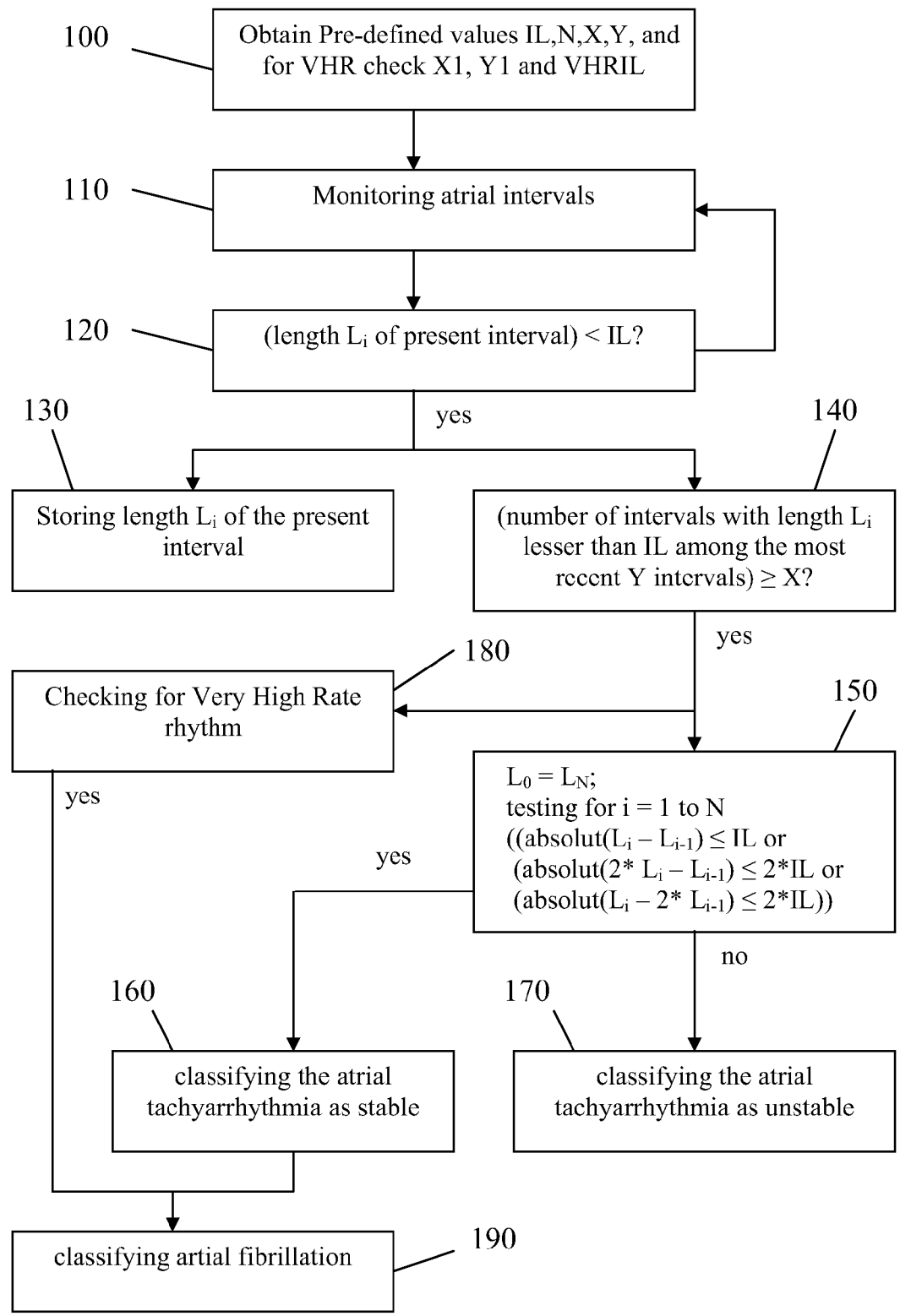
FIG. 1 is a high-level flowchart diagram that illustrates the steps involved in a method for classifying atrial tachyarrhythmia according to a first embodiment.

FIG. 1 shows an example of a first embodiment of the method for classifying atrial tachyarrhythmia according to the invention. In a first step 100 pre-defined values IL, N, X and Y, and for the Very High Rate (VHR) check X1, Y1 and VHRIL are obtained. IL denotes the limit for indicating an atrial interval as being a "tachy-interval", if the length L of the atrial interval is shorter than IL. Numbers X and Y denotes the parameter of the "X-out-of-Y" criterion, i.e. in the scope of the invention atrial tachyarrhythmia is indicated if X among the most recent Y number of intervals have a length L shorter than IL. N denotes the number of "tachy-intervals" which are considered in the stability check 150. VHRIL denotes the Very High Rate Interval Limit. An atrial interval having a length L shorter than IL is incorporated in the VHR check. Numbers X1 and Y1 denotes the parameter of a second "X1-out-of-Y1" criterion, i.e. in the scope of the invention VHR is indicated if X1 among the most recent Y1 number of intervals have a length L shorter than VHRIL.

For classifying atrial intervals as being stable or unstable the atrial intervals are monitored (step 110). Monitoring may be performed continuously or temporarily depending on pre-defined criteria. The length L of monitored atrial intervals are compared with IL in step 120. If it is found that the length $L_i$ of the present interval is shorter than IL, the length $L_i$ of the present interval is stored in step 130. In parallel, in step 140 the "X-out-of-Y" criterion is checked, i.e. it is checked if the number of intervals with length $L_i$ shorter than IL among the most recent Y intervals reach X. If the "X-out-of-Y" criterion is satisfied, atrial tachyarrhythmia is indicated. In this case the method proceeds to step 150 where the stability test is performed. The test considers up to the N most recent length $L_i$ (I=1, 2, . . . , N) stored in step 130. The stability test consists of individual checks performed for each interval length $L_i$ stored in step 130. Each length $L_i$ is compared with the preceding stored length $L_{i-1}$. The rhythm is determined to be stable if all individual checks pass (step 160), the pass criterion are the following:

The difference between the individual interval and the preceding interval does not exceed the stability limit; or The difference between "two times the individual interval" and the preceding interval does not exceed "two times the stability limit"; or The difference between the individual interval and "two times the preceding interval" does not exceed "two times the stability limit".

If an individual interval fails the above check, further testing is aborted and the rhythm is determined to be unstable (step 170).

In a preferred embodiment the storage where the length $L_i$ are stored in step 130 is treated as a ring buffer (RB) during the stability check. In this case $L_0$ is set equal to $L_N$ and the stability check is performed for all individual length in the ring buffer.

In a further embodiment in Step 180 an additional check for Very High Rate rhythm is performed after atrial tachyarrhythmia is indicated in step 140. Y1 intervals stored in step 130 are checked against VHRIL. If programmable X1 number of intervals are found to be shorter than VHRIL, the Very High Rate is indicated for the detected tachyarrhythmia. This is an X1-out-of-Y1 test. In a preferred embodiment Y1 is set equal to N which is the size of RB. Using this indication, an otherwise stable but Very High Rate atrial tachyarrhythmia may optionally be classified in step 190 as atrial fibrillation.

Figure 2:
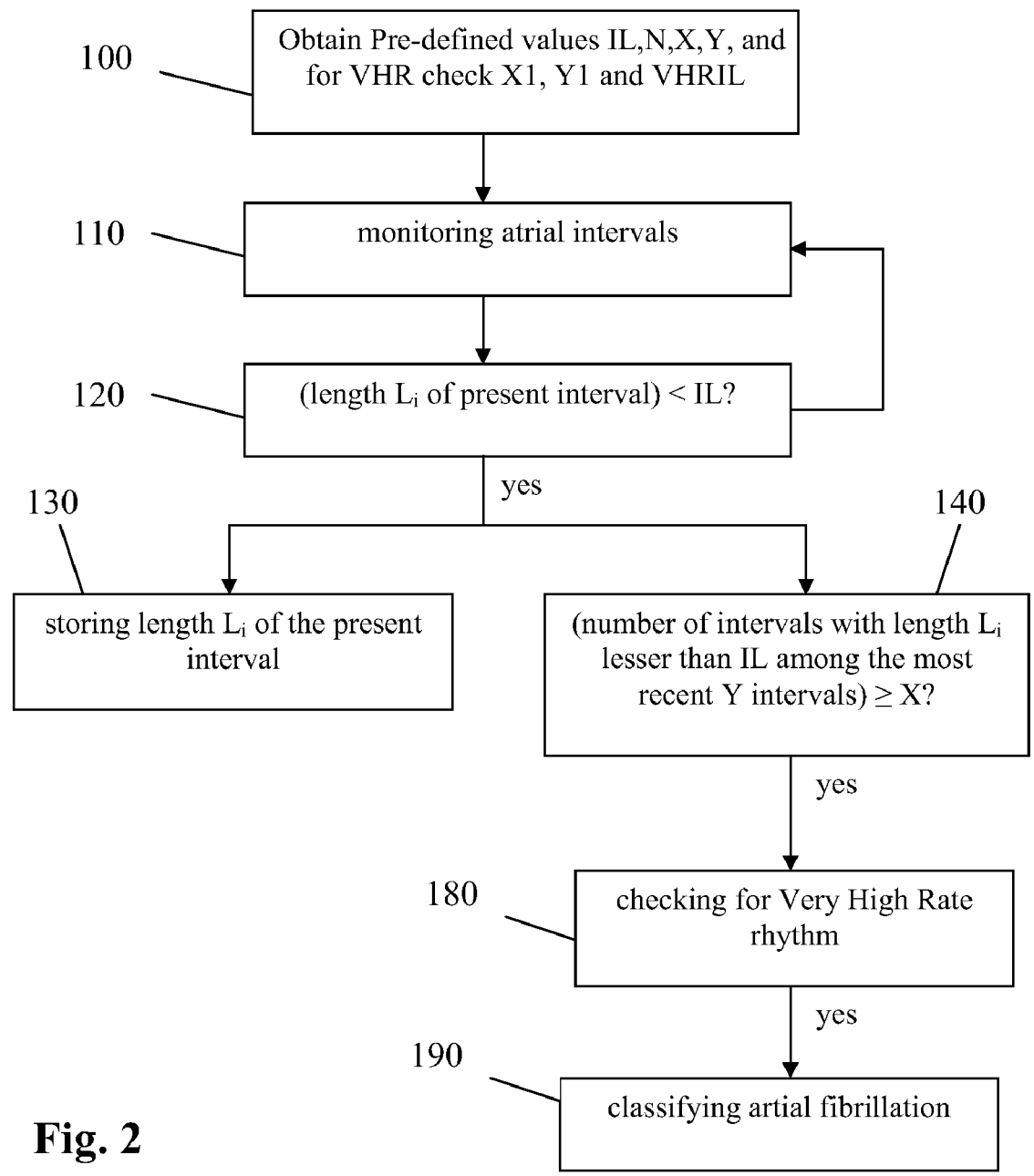
FIG. 2 is a high-level flowchart diagram that illustrates the steps involved in a method for classifying atrial tachyarrhythmia according to a second embodiment.

Turning now to FIG. 2 which illustrates steps of a method similar to the method illustrated in FIG. 1. The difference between FIG. 1 and FIG. 2 consists in that the method shown in FIG. 2 classifies for atrial tachyarrhythmia a Very High Rate rhythm as fibrillation regardless of its stability. Therefore, steps 150, 160 and 170 of the stability test are omitted. The same references indicate the same features.

Figure 3:
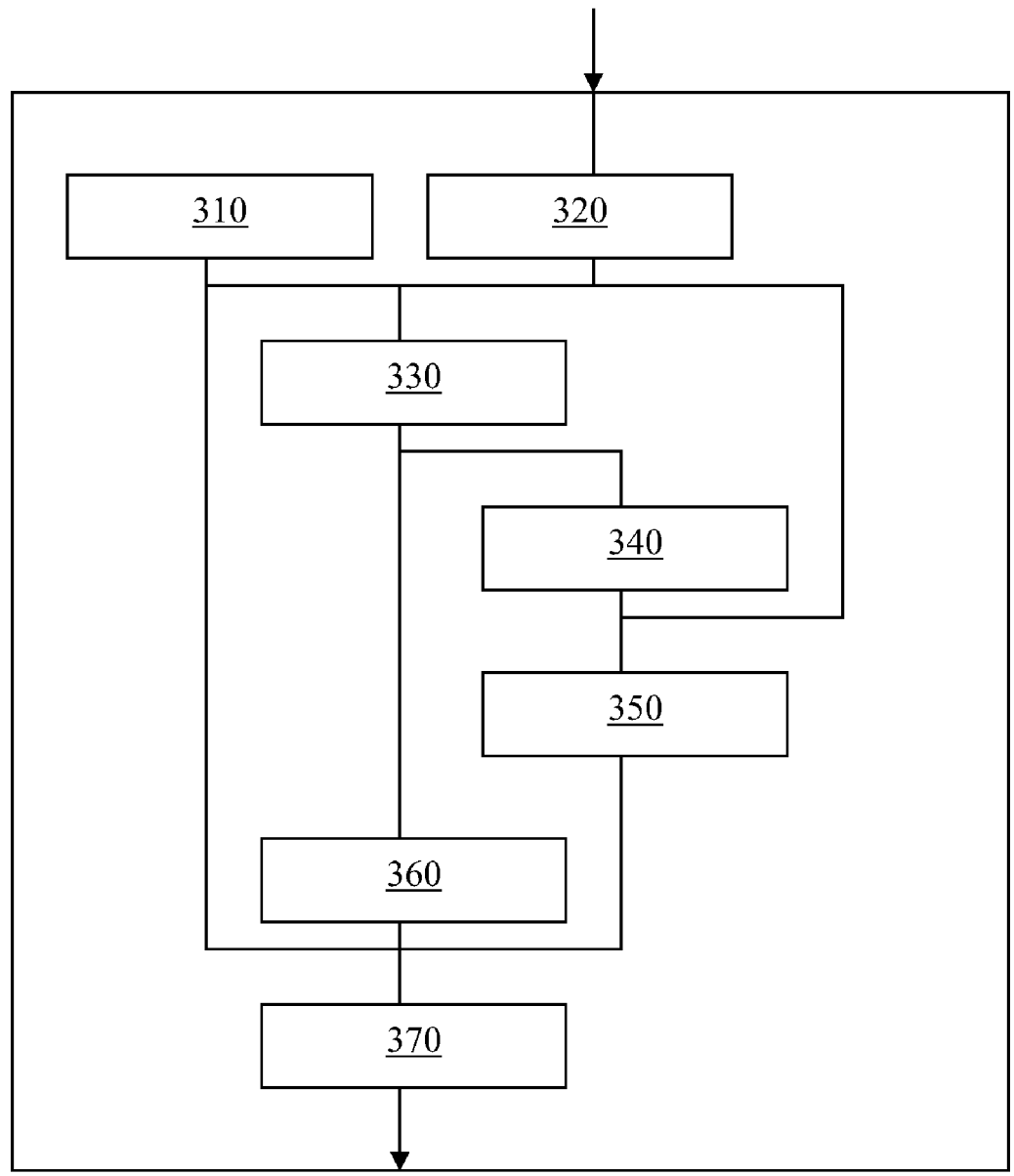
FIG. 3 is a functional block diagram of a device for classifying atrial tachyarrhythmia according to a first embodiment.

FIG. 3 depicts a functional block diagram of a device which is arranged for executing a method for classifying atrial tachyarrhythmia according to the first embodiment. Such a device 300 comprises:

storage means 310 for storing the pre-defined values IL, N, SL, X and Y;

means 320 for monitoring cardiac events;

means 330 for deciding whether an atrial interval has a length shorter than IL or not, the means 330 for deciding being communicatively connected with the storage means 310 and the means 320 for monitoring;

a first FIFO buffer 340 of size Y communicatively connected with the means for deciding 330 for storing flags indicating whether an atrial interval has a length shorter than IL or not;

a counter 350 communicatively connected with the means 320 for monitoring and with the first FIFO buffer 340 for counting atrial intervals with a length shorter than IL among the most recent Y number of atrial intervals;

a second FIFO buffer 360 of size N communicatively connected with the means for deciding 330 for storing the length of atrial interval if the length is shorter than IL; and processing means 370 communicatively connected with the storage means 310, with the counter 350 and with the second FIFO buffer 360 for performing the test and for controlling the device.

Figure 4:
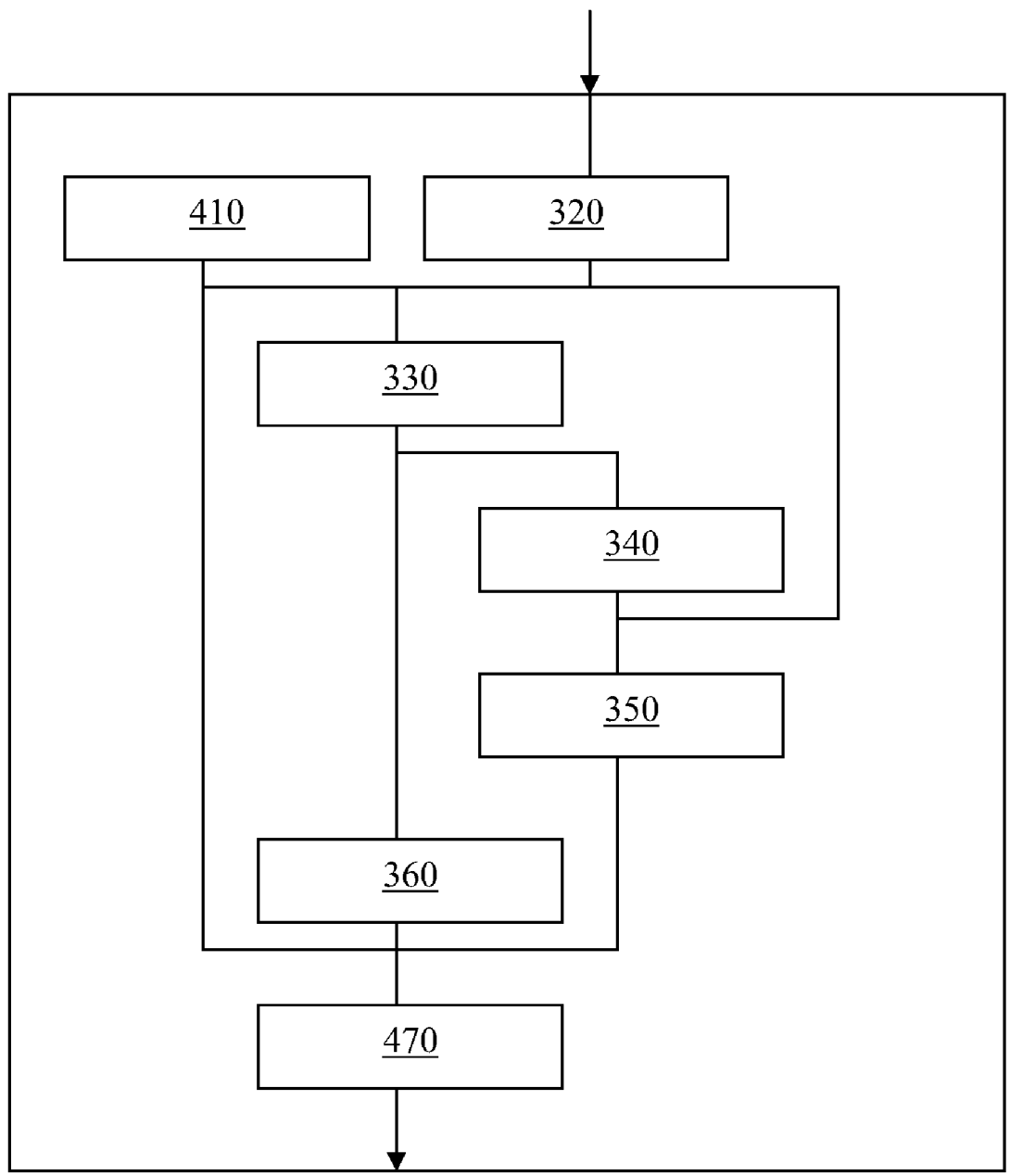
FIG. 4 is a functional block diagram of a device for classifying atrial tachyarrhythmia according to a second embodiment.

FIG. 4 depicts a functional block diagram of a device which is arranged for executing a method for classifying atrial tachyarrhythmia according to the second embodiment. Such a device 400 comprises:

storage means 410 for storing the pre-defined values IL, X, X1, Y, Y1 and VHRIL;

means 320 for monitoring cardiac events;

means 330 for deciding whether an atrial interval has a length shorter than IL or not, the means 330 for deciding being communicatively connected with the storage means 410 and the means 320 for monitoring;

a first FIFO buffer 340 of size Y communicatively connected with the means 330 for deciding for storing flags indicating whether an atrial interval has a length shorter than IL or not;

a counter 350 communicatively connected with the means 320 for monitoring and with the first FIFO buffer 340 for counting atrial intervals with a length shorter than IL among the most recent Y number of atrial intervals;

a second FIFO buffer 360 of size Y1 communicatively connected with the means 330 for deciding for storing the length of atrial interval if the length is shorter than IL; and processing means 470 communicatively connected with the storage means 410, with the counter 350 and with the second FIFO buffer 360 for classifying Very High Rate rhythm and for controlling the device.

Figure 5:
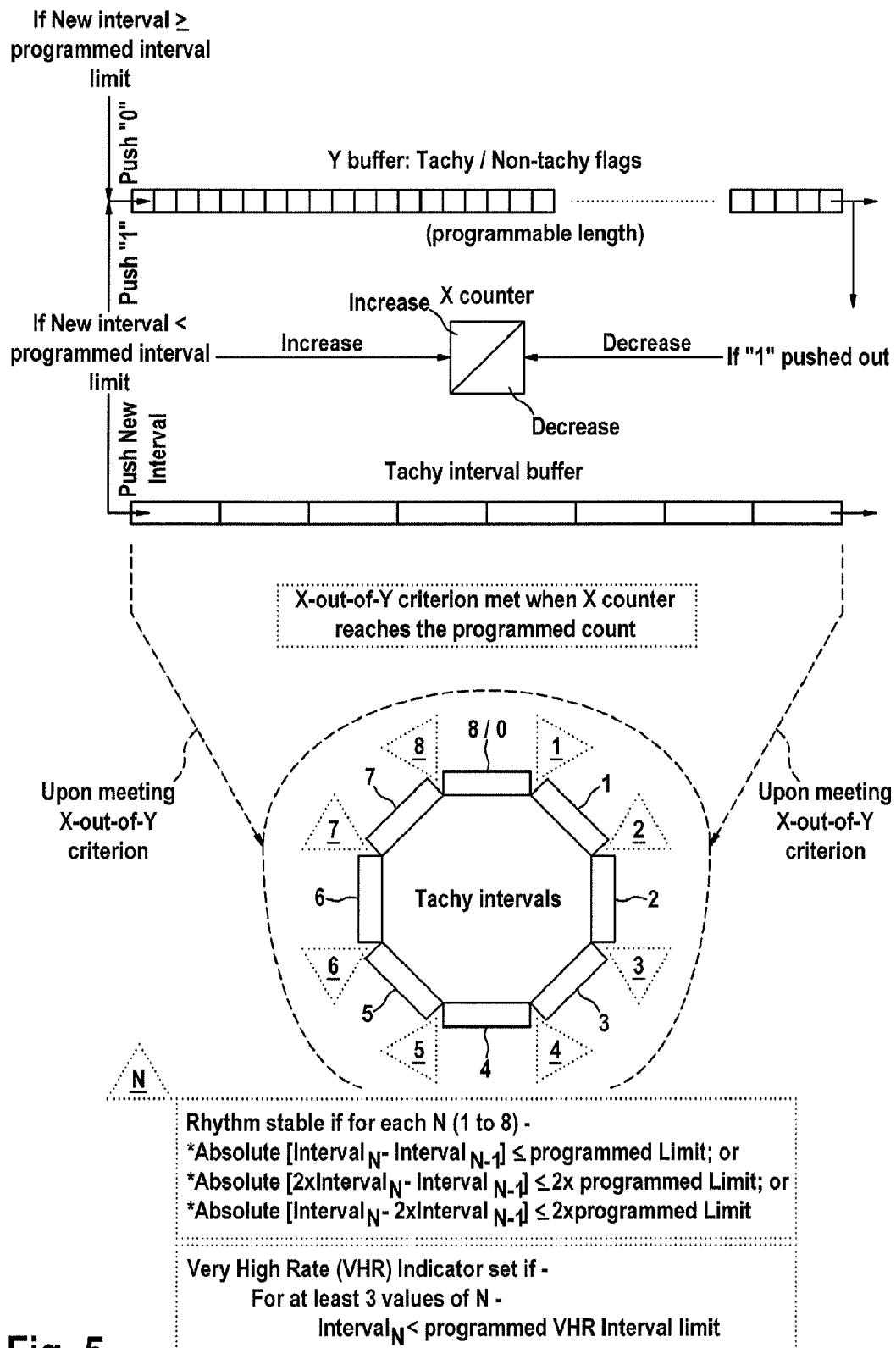
FIG. 5 is a further schematic illustration of an embodiment of a method for classifying atrial tachyarrhythmia where a method for determining Very High rate rhythm is also included.

The internal working of the parts of the devices will become clear with the explanations of FIG. 5. The FIG. 5 illustrates the mechanisms of detecting atrial tachyarrhythmias and of determination of their being stable or unstable. The method of determining a Very High Rate rhythm is also included in FIG. 5.

The "X-out-of-Y" criterion aimed at the detection of atrial tachyarrhythmia uses a FIFO Y-buffer 340 of length Y. The length is preferably programmable, for example by a user defined value Y. Further an up/down X-counter 350 is used. Each new atrial interval is compared with the programmed Interval Limit (IL) and a binary "0" or "1" is pushed into the Y-buffer 340—a "1" if the new interval is shorter than IL, a "0" otherwise. The X-counter 350 is incremented when a "1" is pushed into the Y-buffer 340 and is decremented when a "1" is pushed out of the Y-buffer 340. An atrial tachyarrhythmia is declared when the contents of the X-counter 350 equals the programmed X Count (XC).

Also, when a "1" is pushed into the Y-buffer 340, the new interval is pushed into another FIFO buffer, the Tachy Interval buffer 360. The length of the Tachy Interval buffer 360 is programmable but can not be larger than XC. Upon declaration of an atrial tachyarrhythmia, the Tachy Interval buffer 360 contains the most recent intervals that were found to be shorter than IL. At this time, the Tachy Interval buffer 360 is treated as a Ring Buffer 360a (RB) for performing the stability test.

The stability test consists of individual checks performed for each interval in RB 360a. Each interval is compared with the preceding interval. The most recent interval serves also as the interval preceding the oldest interval thanks to treating the Tachy Interval buffer 360a as a ring buffer for the stability test. The rhythm is determined to be stable if all individual checks pass, the pass criterion being as follows—

The difference between the individual interval and the preceding interval does not exceed the stability limit; or The difference between "two times the individual interval" and the preceding interval does not exceed "two times the stability limit"; or The difference between the individual interval and "two times the preceding interval" does not exceed "two times the stability limit".

If an individual interval fails the above check, further testing is aborted and the rhythm is determined to be unstable.

The intervals in RB 360a are checked against a Very High Rate Interval Limit (VHRIL) corresponding to the programmed Very High Rate limit. This is an X1-out-of-Y1 test where Y1 equals the size of RB 360a. If programmable X1 number of intervals are found to be shorter than VHRIL, the Very High Rate is indicated for the detected tachyarrhythmia.

What is claimed is

1. A method for classifying atrial tachyarrhythmia comprising:
    obtaining pre-defined numbers N, X and Y with N≦X<Y;
    monitoring atrial intervals and comparing a length of each atrial interval with a pre-defined value IL;
    storing a length of atrial interval into a stored length if the length is shorter than IL;
    evaluating the most recent up to N atrial intervals which have a length shorter than IL, in case X among a most recent Y number of atrial intervals are found to have length shorter than IL, and performing for each of the stored length a test with respect to the following criteria:
        an absolute value of a difference between the stored length and its preceding stored length does not exceed a pre-defined value SL,
        an absolute value of a difference between twice the stored length and one time of the preceding stored length does not exceed double of the value SL, and
        an absolute value of a difference between the stored length and twice the preceding stored length does not exceed double of the value SL;
    classifying an atrial tachyarrhythmia into a classification as stable if all tested lengths pass at least one of the criteria; and,
    controlling a cardiac device depending on the classification.

2. The method according to claim 1 further comprising:
    using a first FIFO buffer of size Y and pushing a first flag that indicates tachyarrhythmia in the first FIFO buffer if a length of a monitored atrial interval is shorter than IL, and pushing a second flag that indicates non-tachyarrhythmia in the first FIFO buffer if the length of the monitored atrial interval is equal to or longer than IL.

3. The method according to claim 2 wherein the first flag is a binary "1", and the second flag is a binary "0".

4. The method according to claim 1 further comprising:
    using a counter which is incremented by 1 if a monitored atrial interval has length shorter than IL, and which is decremented by 1 if an atrial interval at the Yth position before the monitored atrial interval has length shorter than IL.

5. The method according to claim 1 further comprising:
    using a second FIFO buffer of size N and storing atrial intervals with lengths shorter than IL into stored atrial intervals in the second FIFO buffer.

6. The method according to claim 5 where the second FIFO buffer is treated as a ring buffer when testing the stored atrial intervals.

7. The method according to claim 1 further comprising:
    performing the test for each of a most recent N stored lengths shorter than IL where the stored length of a most recent atrial interval is also used as a length that precedes an oldest stored length.

8. The method according to claim 1 further comprising:
    obtaining pre-defined values VHRIL, X1 and Y1, and for a most recent Y1 number of atrial intervals which have length shorter than IL, comparing lengths of the most recent Y1 number of atrial intervals with VHRIL and indicating Very High Rate rhythm for a detected tachyarrhythmia if X1 lengths shorter than VHRIL are found.

9. The method according to claim 8 further comprising:
    classifying the atrial tachyarrhythmia as fibrillation if Very High Rate rhythm is indicated.

10. The method according to claim 9 further comprising:
    classifying a stable atrial tachyarrhythmia as fibrillation if Very High Rate rhythm is indicated.

11. The method according to claim 8 where Y1 is set to N.

12. A method for classifying atrial tachyarrhythmia comprising:
    obtaining pre-defined numbers X, X1, Y and Y1 with X<Y and X1<Y1;
    monitoring atrial intervals and comparing a length of each atrial interval with a pre-defined value IL;
    comparing lengths of a most recent Y1 number of atrial intervals which have length shorter than IL with a pre-defined value VHRIL, in case X among the most recent Y number of atrial intervals are found to have a length shorter than IL;
    classifying a classification of Very High Rate rhythm if X1 out of the Y1 number of atrial intervals which have length shorter than IL are found having a length shorter than VHRIL; and,
    controlling a cardiac device depending on the classification.

13. The method according to claim 12 further comprising:
    classifying atrial tachyarrhythmia as fibrillation if Very High Rate rhythm is indicated.

14. The method according to claim 12 further comprising:
    using a first FIFO buffer of size Y and pushing a first flag that indicates tachyarrhythmia in the first FIFO buffer if a length of a monitored atrial interval is shorter than IL, and pushing a second flag that indicates non-tachyarrhythmia in the first FIFO buffer if the length of the monitored atrial interval is equal to or longer than IL.

15. The method according to claim 14 where the first flag is a binary "1", and the second flag is a binary "0".

16. The method according to claim 12 further comprising:
    using a counter which is incremented by 1 if a monitored atrial interval has length shorter than IL, and which is decremented by 1 if an atrial interval at the Yth position before the monitored atrial interval has length shorter than IL.

17. A device for classifying atrial tachyarrhythmia comprising control and storage means, the device being configured to:
    obtain pre-defined numbers N, X and Y with N≦X<Y;
    monitor atrial intervals and compare a length of each atrial interval with a pre-defined value IL;
    store a length of an atrial interval into a stored length if the length is shorter than IL;
    evaluate a most recent up to N intervals which have length shorter than IL in case X among a most recent Y number of atrial intervals are found to have length shorter than IL, and perform for each of the stored length a test with respect to the following criteria:
        an absolute value of a difference between the stored length and its preceding stored length does not exceed a pre-defined value SL,
        an absolute value of a difference between twice the stored length and one time of the preceding stored length does not exceed double of the value SL, and
        an absolute value of a difference between the stored length and twice the preceding stored length does not exceed double of the value SL;

classify an atrial tachyarrhythmia into a classification as stable if all of the tested lengths pass at least one of the criteria; and
control a cardiac device depending on the classification.

18. The device according to claim 17, where the device is an implantable cardiac device, such as a pacemaker, a defibrillator or a cardioverter.

19. The device according to claim 17, further comprising:
said storage means configured to store the pre-defined values N, X, Y and pre-defined values IL and SL;
monitoring means to monitor cardiac events;
deciding means to decide whether an atrial interval has a length shorter than IL or not, wherein the deciding means is communicatively connected with the storage means and the monitoring means;
a first FIFO buffer of size Y communicatively connected with the deciding means and configured to store flags that indicate whether an atrial interval has a length shorter than IL or not;
a counter communicatively connected with the monitoring means and with the first FIFO buffer and configured to count atrial intervals with a length shorter than IL among the most recent Y number of atrial intervals;
a second FIFO buffer of size N communicatively connected with the deciding means and configured to store a length of atrial interval if the length is shorter than IL; and
processing means communicatively connected with the storage means, with the counter and with the second FIFO buffer and configured to perform the test and for control the device.

20. The device according to claim 19, wherein the second FIFO buffer is at least temporarily treated as a ring buffer.

21. A device for classifying atrial tachyarrhythmia comprising control and storage means, the device being configured to:
obtain pre-defined numbers X, X1, Y and Y1 with X<Y and X1<Y1;
monitor atrial intervals and compare a length of each atrial interval with a pre-defined value IL;
compare lengths of a most recent Y1 number of atrial intervals which have a length shorter than IL with a pre-defined value VHRIL, in case X among a most recent Y number of atrial intervals are found to have a length shorter than IL;
classify a Very High Rate rhythm into a classification if X1 out of the Y1 number of atrial intervals which have a length shorter than IL are found having a length shorter than VHRIL; and,
control a cardiac device depending on the classification.

22. The device according to claim 21, where the device is an implantable cardiac device, such as a pacemaker, a defibrillator or a cardioverter.

23. The device according to claim 21, further comprising:
said storage means configured to store the pre-defined values X, X1, Y, Y1 and pre-defined values IL and VHRIL;
monitoring means to monitor cardiac events;
deciding means to decide whether an atrial interval has a length shorter than IL or not, wherein the deciding means are communicatively connected with the storage means and the monitoring means;
a first FIFO buffer of size Y communicatively connected with the deciding means and configured to store flags that indicate whether an atrial interval has a length shorter than IL or not;
a counter communicatively connected with the monitor means and with the first FIFO buffer and configured to count atrial intervals with a length shorter than IL among the most recent Y number of atrial intervals;
a second FIFO buffer of size Y1 communicatively connected with deciding means and configured to store the length of atrial interval if the length is shorter than IL; and
processing means communicatively connected with the storage means, with the counter and with the second FIFO buffer and configured to classify Very High Rate rhythm and for control the device.

24. A computer-readable storage medium that stores program code for a data processing device wherein said program code is configure to:
obtain pre-defined numbers N, X and Y with $N \leq X < Y$;
monitor atrial intervals and compare a length of each atrial interval with a pre-defined value IL;
store a length of an atrial interval into a stored length if the length is shorter than IL;
evaluate a most recent up to N intervals which have length shorter than IL in case X among a most recent Y number of atrial intervals are found to have length shorter than IL, and perform for each of the stored length a test with respect to the following criteria:
an absolute value of a difference between the stored length and its preceding stored length does not exceed a pre-defined value SL,
an absolute value of a difference between twice the stored length and one time of the preceding stored length does not exceed double of the value SL, and
an absolute value of a difference between the stored length and twice the preceding stored length does not exceed double of the value SL;
classify an atrial tachyarrhythmia into a classification as stable if all of the tested lengths pass at least one of the criteria; and
control a cardiac device depending on the classification.

25. A computer-readable storage medium that stores program code for a data processing device wherein said program code is configure to:
obtain pre-defined numbers X, X1, Y and Y1 with X<Y and X1<Y1;
monitor atrial intervals and compare a length of each atrial interval with a pre-defined value IL;
compare lengths of a most recent Y1 number of atrial intervals which have a length shorter than IL with a pre-defined value VHRIL, in case X among a most recent Y number of atrial intervals are found to have a length shorter than IL;
classify a Very High Rate rhythm into a classification if X1 out of the Y1 number of atrial intervals which have a length shorter than IL are found having a length shorter than VHRIL; and,
control a cardiac device depending on the classification.

* * * * *